(12) United States Patent
Boira Bonhora et al.

(10) Patent No.: US 11,850,315 B2
(45) Date of Patent: Dec. 26, 2023

(54) DEVICE AND METHOD FOR STERILIZING FLEXIBLE BAGS BY ELECTRON BEAM IRRADIATION

(71) Applicant: GRIFOLS ENGINEERING, S.A., Parets del Valles (ES)

(72) Inventors: Jordi Boira Bonhora, Parets del Valles (ES); Daniel Fleta Coit, Parets del Valles (ES); Carlos Roura Salietti, Parets del Valles (ES)

(73) Assignee: GRIFOLS ENGINEERING, S.A.

( * ) Notice: Subject to any disclaimer, the term of this patent is extended or adjusted under 35 U.S.C. 154(b) by 16 days.

(21) Appl. No.: 16/833,457

(22) Filed: Mar. 27, 2020

(65) Prior Publication Data

US 2020/0324004 A1    Oct. 15, 2020

(30) Foreign Application Priority Data

Apr. 12, 2019  (EP) ..................... 19382282

(51) Int. Cl.
*A61L 2/08* (2006.01)
*A61J 1/10* (2006.01)

(52) U.S. Cl.
CPC ............. *A61L 2/087* (2013.01); *A61J 1/10* (2013.01); *A61L 2202/23* (2013.01)

(58) Field of Classification Search
CPC .......... A61L 2/087; A61L 2202/23; A61J 1/10
See application file for complete search history.

(56) References Cited

U.S. PATENT DOCUMENTS

| | | | |
|---|---|---|---|
| 8,795,599 B2 | 8/2014 | Fontcuberta | |
| 10,625,894 B2 | 4/2020 | Boira Bonhora | |
| 2005/0112248 A1* | 5/2005 | Galloway | A23L 3/32 426/237 |
| 2012/0114524 A1 | 5/2012 | Sigg | |
| 2020/0000948 A1 | 1/2020 | Bonhora | |

FOREIGN PATENT DOCUMENTS

| | | |
|---|---|---|
| EP | 3721909 A1 | 10/2020 |
| ES | 2549694 A1 | 10/2015 |
| ES | 1180709 U | 4/2017 |
| JP | 2002-000705 A | 1/2002 |
| JP | 2002000705 A | 1/2002 |
| UY | 37276 A | 8/2017 |
| WO | WO 2018/167334 A1 | 9/2018 |
| WO | WO 2018167334 A1 | 9/2018 |

OTHER PUBLICATIONS

Search Report dated Feb. 15, 2021 in Chilean Application No. 2020-00941.
Extended European Search Reported, dated Oct. 25, 2019, in European Application No. 19382282.2.

\* cited by examiner

*Primary Examiner* — Timothy C Cleveland
(74) *Attorney, Agent, or Firm* — Knobbe, Martens, Olson & Bear LLP

(57) ABSTRACT

An device is for electron-beam irradiation sterilization of flexible bags that may contain human plasma protein solutions for therapeutic use. The device has two electron accelerators, a first accelerator emitting an electron beam with energies between 400 and 500 keV and a second accelerator emitting an electron beam with an energy of at least 4 MeV. A sterilization method by electron-beam irradiation provides sterilization of such flexible bags. An in-line filling process for flexible bags can use the sterilization device and method.

7 Claims, 6 Drawing Sheets

DEVICE AND METHOD FOR STERILIZING FLEXIBLE BAGS BY ELECTRON BEAM IRRADIATION

PRIORITY AND CROSS-REFERENCE TO RELATED APPLICATIONS

This application claims the benefit of European Application No. EP 19382282.2, filed on Apr. 12, 2019, which is hereby incorporated by reference in its entirety.

FIELD

This invention relates to the pharmaceutical sector, specifically to an improved device for sterilizing flexible bags, in particular the type of flexible bags that may contain human plasma protein solutions for therapeutic use. In addition, the present invention relates to a sterilization method for such flexible bags by electron-beam irradiation and to an in-line filling method for flexible bags using the sterilization device and method of the present invention.

BACKGROUND

Electron-beam irradiation, also known as "E-beam", is a form of ionising radiation which is generally characterised by low penetration and high doses of applied energy. Said beam is a stream of concentrated and highly charged electrons. These electrons are generated by an accelerator capable of producing beams which may be continuous or pulsed. The material to be sterilized absorbs the energy of the electrons and said energy absorption, also known as absorbed dose, eliminates microorganisms by destroying their DNA strands.

SUMMARY

This invention relates to the pharmaceutical sector, specifically to an improved device for electron-beam irradiation sterilization of flexible bags, in particular the type of flexible bags that may contain human plasma protein solutions for therapeutic use. This device comprises two electron accelerators: a first accelerator emitting an electron beam with energies between 400 and 500 keV and a second accelerator emitting an electron beam with an energy of at least 4 MeV. In addition, the present invention relates to a sterilization method by electron-beam irradiation of such flexible bags and to an in-line filling process for flexible bags using the sterilization device and method of this invention.

BRIEF DESCRIPTION OF THE DRAWINGS

The invention will be explained below in connection to the figures, where.

DETAILED DESCRIPTION

Figure 1:
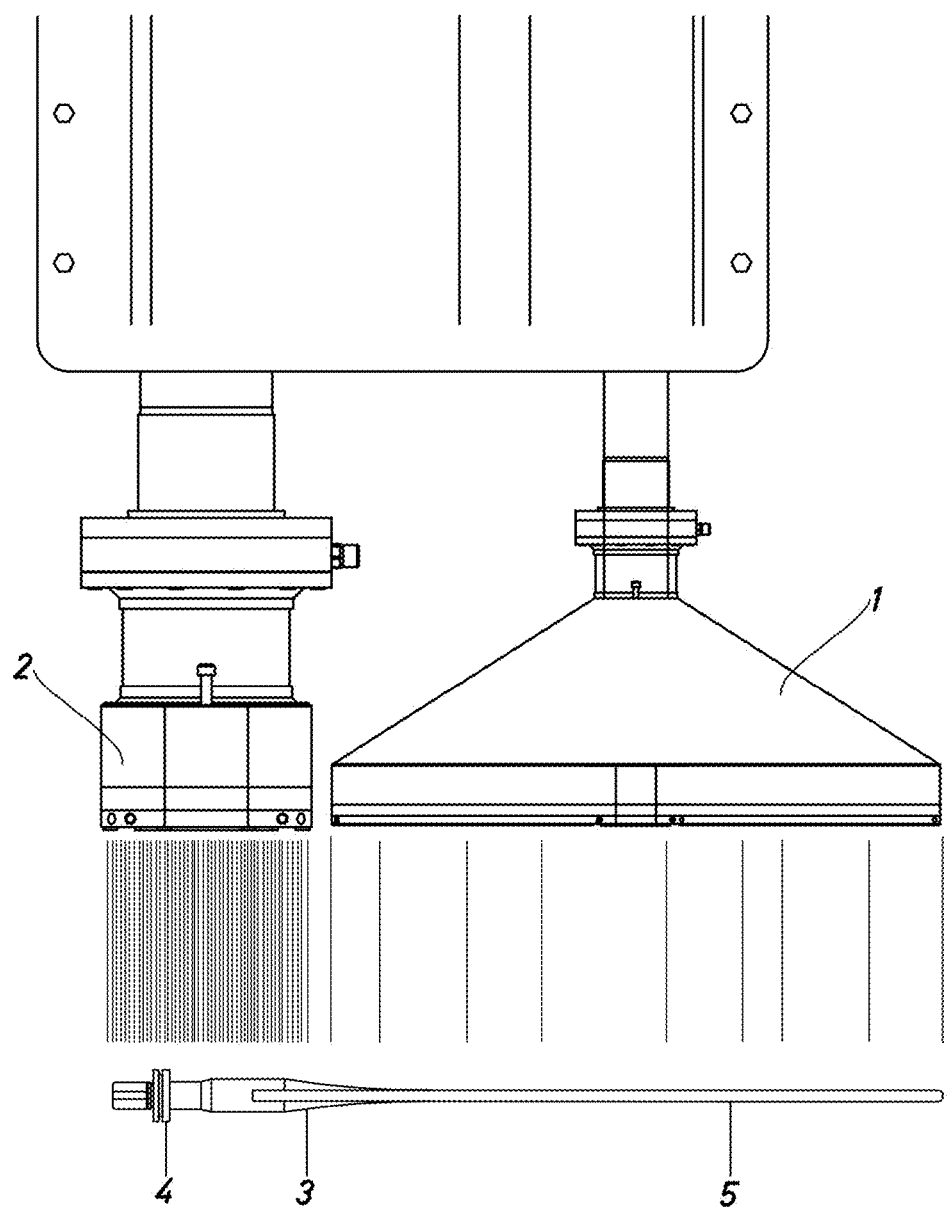
FIG. 1 is a front view of one embodiment of the electron-beam sterilization device according to the present invention.

Commercial electron-beam accelerator equipment typically operates with a single energy, and in the case of pharmaceutical product sterilization, a high energy electron-beam is typically required to achieve product and packaging penetration. A higher energy of the electron beam will cause a higher penetration of the electron beam into the product.

When the electron beam is assessed in order to carry out a sterilization method, different parameters such as product density, size, orientation and packaging must be considered. Generally, E-beam irradiation works better when used on low-density and uniformly packaged products.

In the specific case of flexible bags suitable for containing a solution of human plasma proteins, these are made up of various materials and thicknesses. For example, the bag walls can be as thick as approximately 130 μm, the tube of the outlet port of the bag, which is sealed to it, can be 1.24-mm thick, while the twist-off cap is the thickest area, which can be approximately 3 mm. All these parts must be decontaminated and sterilized before filling in the bags with these human plasma protein solutions. Bags suitable for sterilizing with the device of the present invention are those disclosed in the Spanish Patent application No. ES201431561.

The patent application No. ES201730338 discloses a device for flexible bag sterilization which comprises an accelerator emitting an electron beam with energies between 450 and 500 keV and an accelerator emitting another electron beam with energies between 700 and 750 keV. The bags are vertically placed and both electron guns are facing each other, and the beam is shot parallel to the ground.

The inventors of this invention have discovered that using energies between 700 and 750 keV, and even up to 2 MeV, in the higher energy electron beam, is not enough to sterilize the caps of such flexible bags, due to the fact that some internal parts of them remain unsterilized, and they can later be in contact with the pharmaceutical product that will contain the bag. This is due to the fact that since the accelerators are on one side of the bag, radiation needs to cross a distance not only from the cap thickness in the area closest to the electron accelerators, but also from the cap thickness in the furthest part of such accelerators.

After an extensive investigation it has been determined that, in order to overcome the above-mentioned drawbacks, it is necessary for this electron beam to have an energy equal to or greater than 4 MeV, that is to say, at least 5 times higher than the energy known in the current state of the art.

Surprisingly, the inventors were able to use a combination of novel features that make the device of this invention both very effective and safe. The inventors have determined that in the device of this invention, accelerators should not be opposed to each other, because such radiation would cause damage to the accelerators themselves, and should emit the electron beam perpendicularly and in the direction to the ground, since the possibility of radiation escaping into the surrounding environment is very high when the emissions are parallel to the ground, with consequences both for humans and the surrounding environment. The position of the bag to be sterilized, which will be parallel to the ground, has also been modified. In addition, containment measures have been taken to prevent the escape of radiation. Therefore, the inventors of the present invention have developed an electron beam sterilization device that overcomes the disadvantages of the prior art, in which both accelerators are arranged at the top of the device thus allowing the emission of the electron beam downwards, in a direction perpendicular to the ground, with the bag parallel to the ground and with additional containment measures so that radiation will not escape.

Steriliz

In a first aspect, this invention relates to a device for the sterilization of flexible bags characterised in that it comprises a sterilization zone comprising two electron accelerators: a first electron accelerator, which emits an electron beam with energies between 400 and 500 keV and a second electron accelerator, which emits an electron beam with an energy of at least 4 MeV, preferably between 4 and 5 MeV, most preferably of 4 MeV.

In one embodiment, the device of the present invention is arranged in a radiation-proof area, in which measures have been taken to contain the radiation emitted by the accelerators. Said containment measures can be both walls and floor, the walls must be at least 65-cm thick, preferably between 65 and 80 cm, and preferably made of lead. The floor can be made of the same thickness and material as the walls.

FIG. 1 shows a front view of the sterilization zone of one embodiment of the sterilization device according to the present invention. Said sterilization zone is formed by one accelerator or emitter of electron beams of lower energy -1- (400-500 keV), one accelerator or emitter of electron beams of higher energy than the previous one -2- (4-5 MeV) and a flexible bag -3- to be sterilized that includes two areas: the port-twist-off stopper structure -4- and the body -5- of the bag. In this embodiment, both accelerators are arranged at the top of the device and shoot their electron beams downwards, in a direction perpendicular to the ground. The lower energy accelerator -1- shoots electron beams towards the body zone -5- of the bag, while the higher energy accelerator -2- shoots electron beams towards the port-twist-off stopper -4- of the bag.

Figure 2:
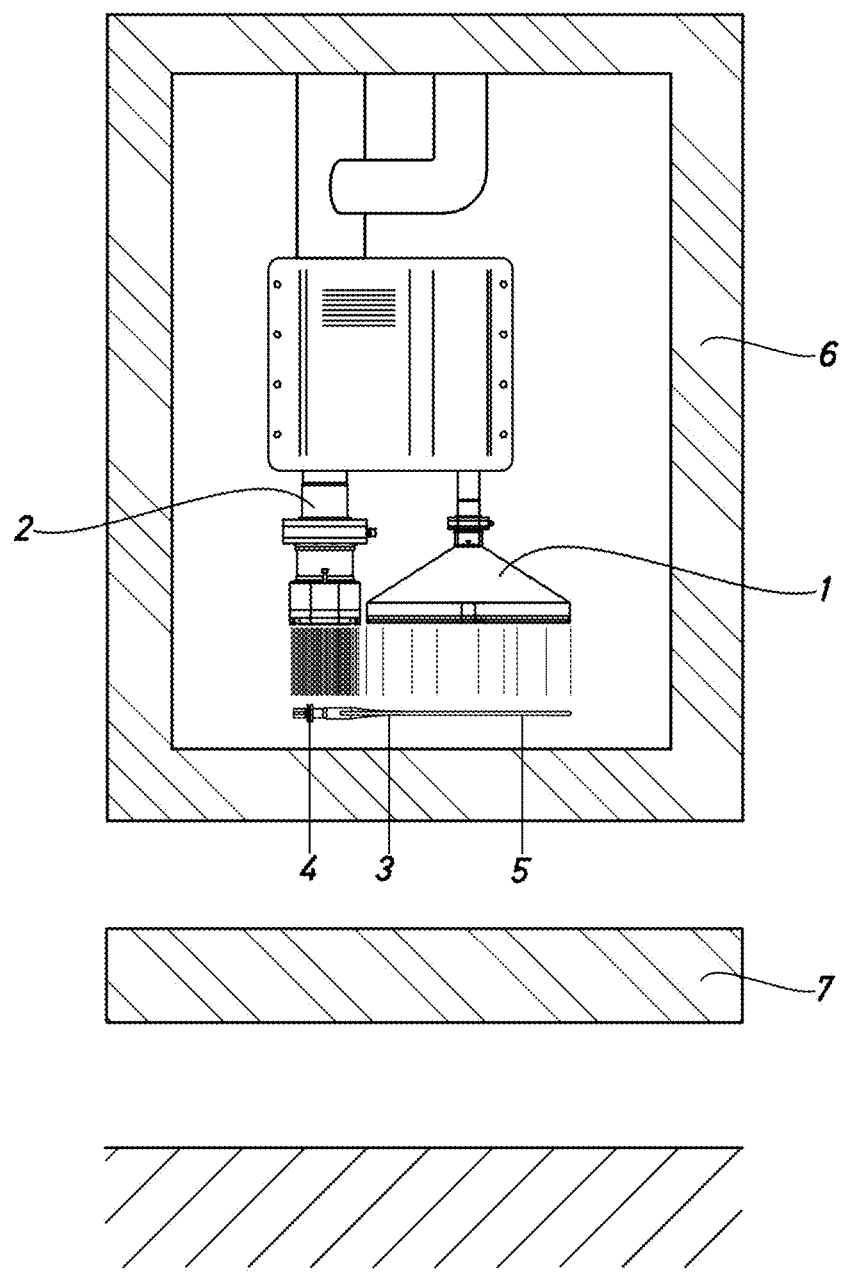
FIG. 2 is a front view of one embodiment of the electron-beam sterilization device according to the present invention with protective measures against the escape of radiation.

FIG. 2 shows a front view of the sterilization zone of one embodiment of the sterilization device according to the present invention. Said sterilization zone consists of one accelerator or emitter of electron beams with lower energy -1- (400-500 keV), one accelerator or emitter of electron beams with higher energy than the previous one -2- (4-5 MeV) and a flexible bag -3- to be sterilized which comprises two areas: the port-twist-off stopper structure -4- and the body -5- of the bag. In this embodiment, both accelerators are arranged at the top of the device and shoot their electron beams downwards, in a direction perpendicular to the ground. In addition, protective measures can be observed on both walls -6- and the floor -7- that surround the device of this invention. In one embodiment, the walls -6- of the device of this invention are at least 65-cm thick, preferably between 65 and 80 cm. Preferably, the weight of the containment measures of the device of this invention must be of at least 40 tons, and the material is preferably lead.

Figure 3:
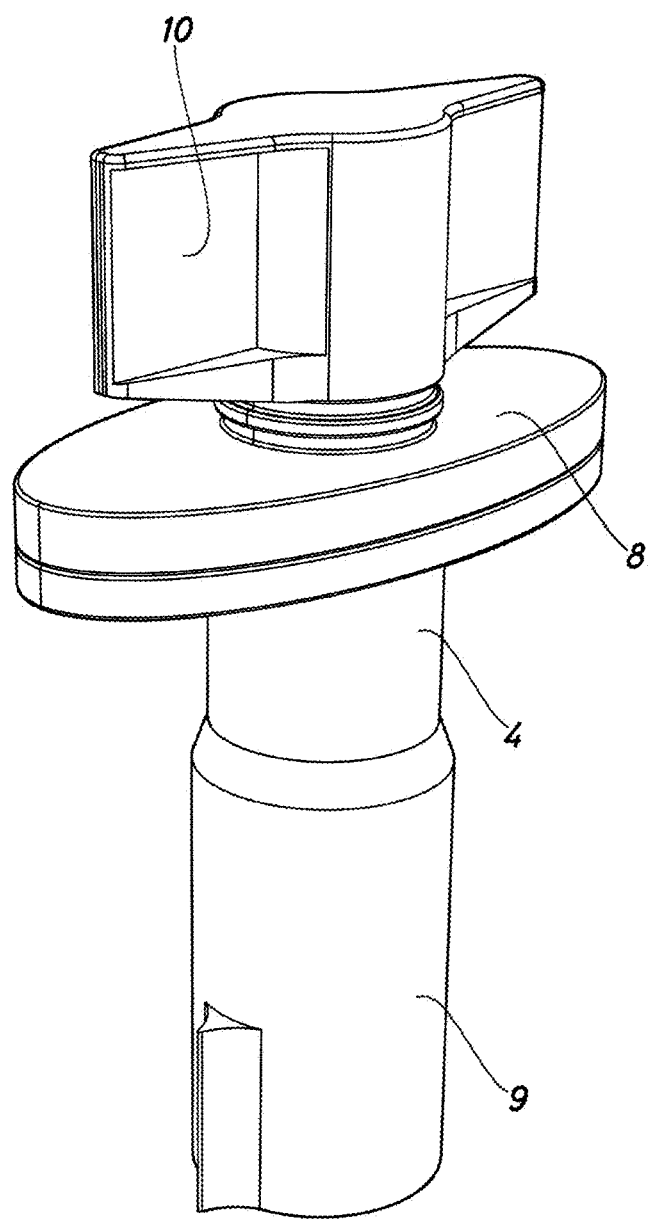
FIG. 3 is a view in perspective of one embodiment of a twist-off stopper-port structure of a flexible bag to be sterilized with the device of the present invention.

FIG. 3 shows a view in perspective of a port-twist-off stopper structure -4- of a flexible bag to be sterilized. This port-twist-off stopper structure -4- normally consists of a twist-off stopper -8- and a port -9-. The twist-off stopper -8- has an activation key -10- in its upper part, which normally has a weakened zone in its contact with the rest of the twist-off stopper -8- structure, which therefore, can be removed and activated by the user by means of a mechanical action, for example, by rotation, at the moment the bag is intended to be used.

Figure 4:
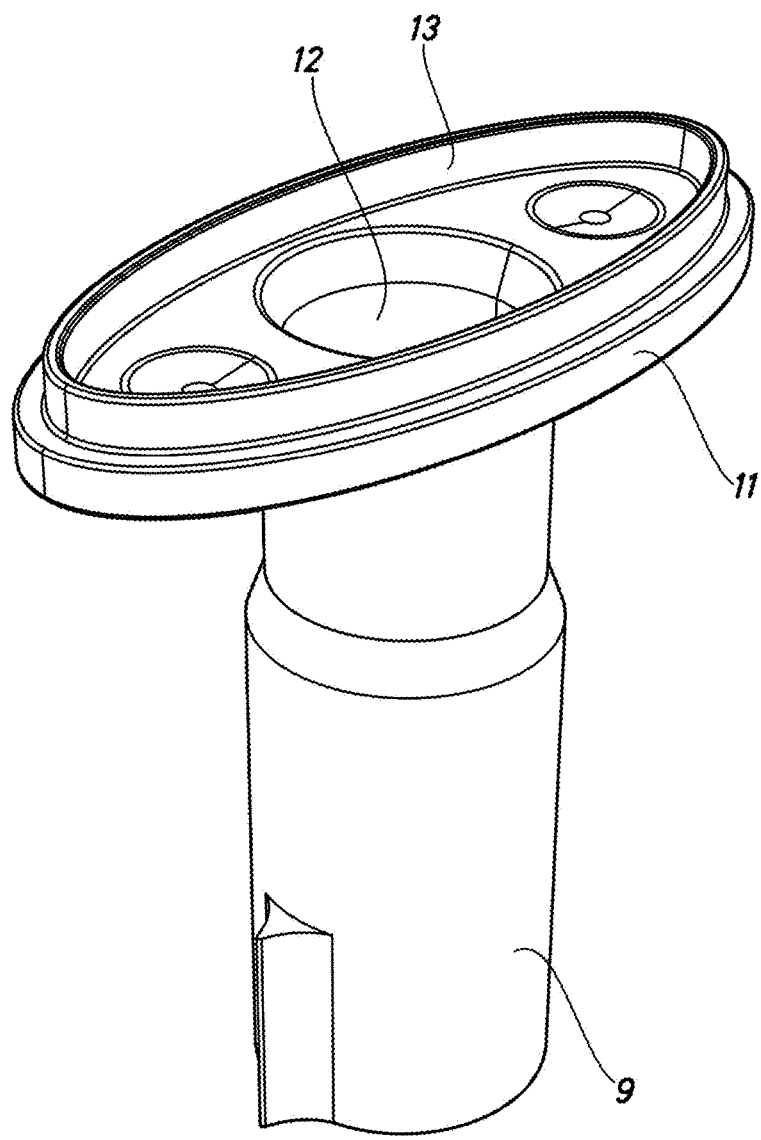
FIG. 4 shows a view in perspective of the port-twist-off stopper structure of FIG. 3.

FIG. 4 shows a view in perspective of the port -9- of the port-twist-off stopper structure -4- of FIG. 3. This port -9- has an oval-shaped flange -11-, which has an upper surface with a continuous protrusion -13- that runs the periphery of its upper surface describing the same oval shape as the flange -11-. In the centre of the flange, there is a channel -12- through which the product to be contained by the flexible bag will pass.

In another aspect, the present invention discloses a method for sterilizing flexible bags containing a solution of human plasma proteins that uses the electron beam accelerator device mentioned above. Such method is characterized in that it comprises the following steps:

a) at least one emission of an electron beam with energies of 400-500 keV made by a first electron accelerator;
b) after approximately 10 nsec to 1.5 sec, emission of a second electron beam by a second electron accelerator with an energy of at least 4 MeV.

Preferably, the energy of this second electron accelerator is between 4 and 5 MeV, most preferably being 4 MeV.

In one embodiment of the electron beam accelerator device of the present invention, the distance from the flexible bag to be sterilized to the irradiation source is between 1.5 cm and 7 cm. Preferably, such distance is 4 cm.

The sterilization method of the present invention may be carried out before or after the filling of the bag and it is preferably made in a sterile room.

The flexible bag to be sterilized by the method of the present invention may be made from any of the materials appropriate for the pharmaceutical industry known in the state of the art. Flexible bags that can be sterilized with the method of this invention can have a volume of 50 mL to 500 mL.

Additionally, such flexible bag may contain pharmaceutical solutions of biological origin, such as blood or blood products, such as plasma, serum, red blood cells, albumin, α-1-antitrypsin, von Willebrand factor, coagulation factors including factor VII, factor VIII and factor IX, immunoglobulins, plasminogen, plasmin, antithrombin III, fibrinogen, fibrin, thrombin or combinations thereof. It is also considered that the pharmaceutical product or liquid may not be of biological origin but obtained by any other procedure or method known in the state of the art, e.g. chemical synthesis, recombinant production or transgenic production.

In a last aspect, the present invention relates to an in-line filling method for flexible bags of human plasma proteins, comprising a step of sterilization by means of electron beams with a device as mentioned above.

Such in-line filling process for flexible bags comprises the following steps:

a) bag formation and thermo-printing;
b) sterilization of the bags by electron beam, in accordance with the method described above;
c) filling of the bags with the human plasma protein solution in a sterile setting; and
d) sealing of bags.

In the said in-line process, the formation of the bags is carried out from coils where the film that will form the wall of the bags is rolled into tube shapes and to which the port-twist-off stopper structure is attached and welded. Subsequently, the bags are identified by means of thermo printing on the surface thereof.

The flexible bags that can be sterilized with the method of this invention may have a volume of 50 mL to 500 mL.

Additionally, said flexible bags may contain pharmaceutical solutions of biological origin, such as blood or blood products, such as plasma, serum, red blood cells, albumin, a 1 antitrypsin, von Willebrand factor, coagulation factors including factor VII, factor VIII and factor IX, immunoglobulins, plasminogen, plasmin, antithrombin III, fibrinogen, fibrin, thrombin or combinations thereof. It is also considered that the pharmaceutical product or liquid may not be of biological origin but obtained by any other procedure or method known in the state of the art, e.g. chemical synthesis, recombinant production or transgenic production.

For a better understanding, this invention is described below in reference to the following example, which in no case is intended to limit the present invention.

EXAMPLE. Determination of the highest electron beam energy needed to sterilize the twist-off stopper of the flexible bag.

Bags produced by Laboratorios Grifols S. A. with four different volumes (50, 100, 250 and 500 mL) were tested. However, the thicknesses of all the bags are the same in all four formats, the characteristics of which are summarised in Table 1 below. The walls of the bags consist of a multi-layer film in which the different layers are joined together by a layer of adhesive.

TABLE 1

Characteristics of the flexible bag walls.

| Bag | Layer 1 (PET-SiO) | Layer 2 (OPA) | Layer 3 (PP-SiO) | Layer 4 (PP) |
|---|---|---|---|---|
| Formulation | $C_{10}H_8O_4SiO$ | $C_8H_6O_2$ | $C_3H_6SiO$ | $C_3H_6$ |
| Density (g/cm$^3$) | 1.42 | 1.13 | 0.889 | 0.894 |
| Thickness (μm) | 12 | 15 | 18 | 85 |

Figure 5:
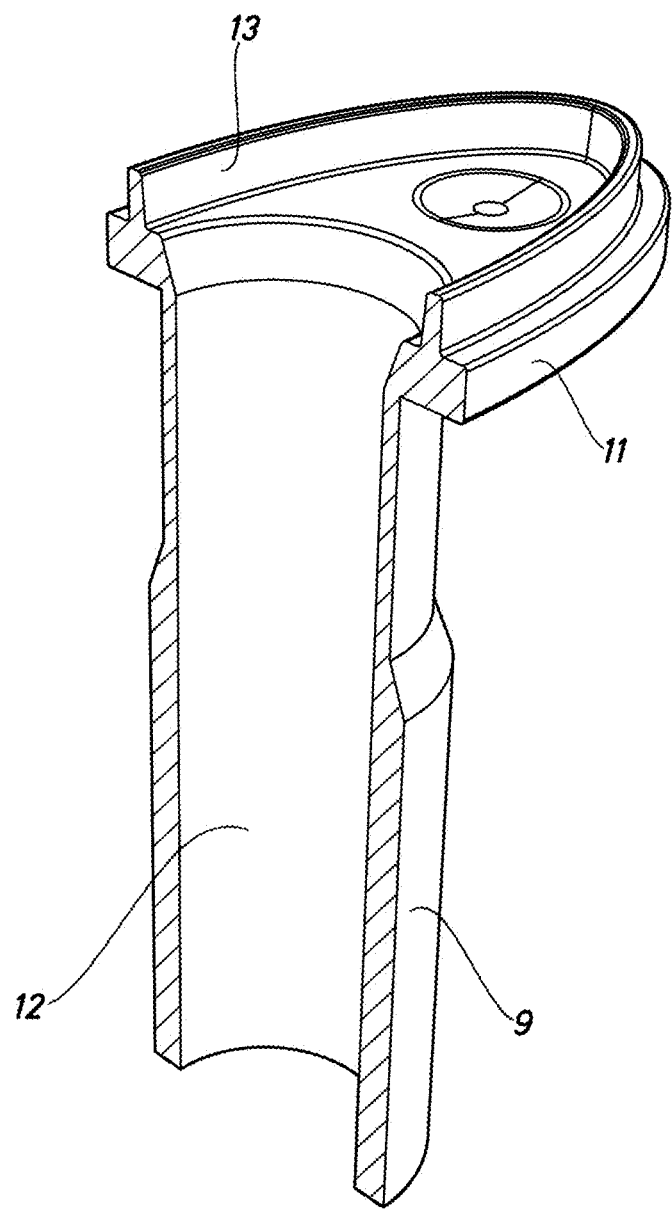
FIG. 5 shows a view in perspective of the port of FIG. 4 both transverse and longitudinally sectioned.

The total wall thickness of the bag is 130 μm, not taking into consideration the intermediate layers of adhesive which can be as thick as ±12 μm. On the other hand, the thickness of the twist-off stopper was measured, and a total thickness of 2.85 mm was obtained. The smaller diameter of the oval shape forming the flange -11- of the port -9- of the port-twist-off stopper structure is approximately 16 mm, as shown in FIG. 5.

Figure 6:
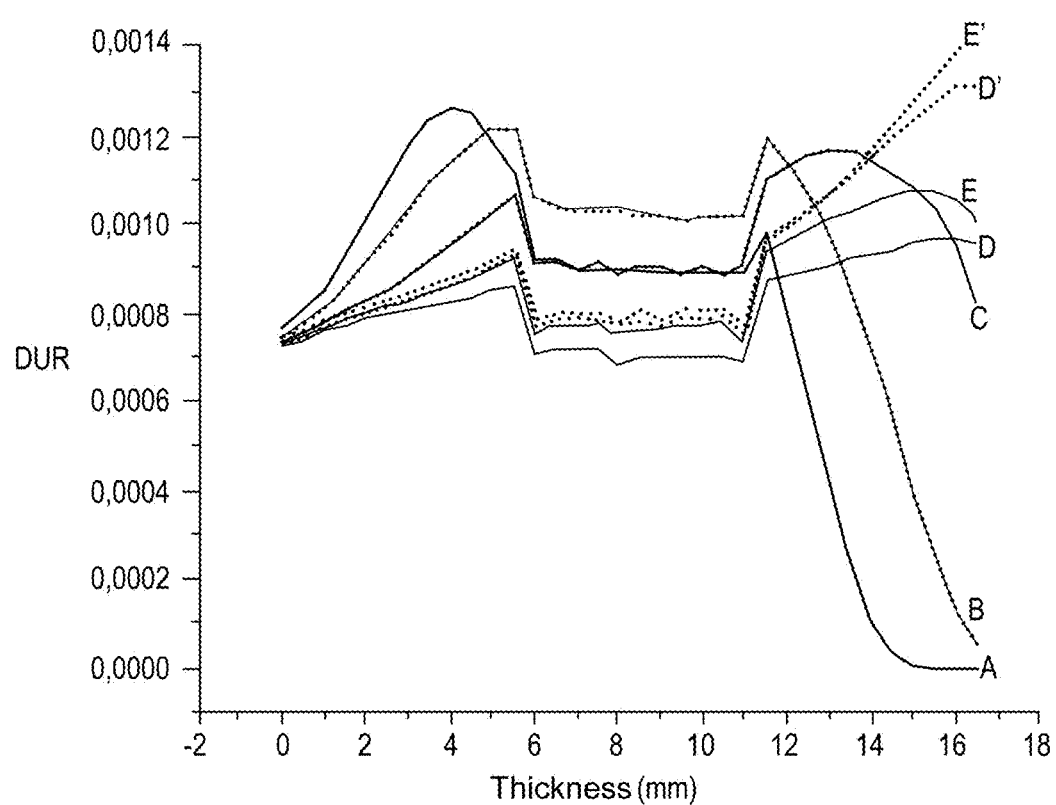
FIG. 6 shows a graph depicting the dose uniformity ratio (DUR), which indicates the ratio between the maximum dose and the minimum dose applied to a material, of different electron beams as a function of the distance run through the smaller diameter of the oval shape which makes up the flange of the port in FIG. 5.

Five energies from the highest energy electron beam were chosen for this study: 1.8 MeV (curve A in FIG. 6), 2.2 MeV (curve B), 3 MeV (curve C), 4 MeV (curve D) and 5 MeV (curve E), represented in FIG. 6. The last two were also fitted with a collector, which is a stainless-steel plate represented in curves D' and E' in FIG. 6.

As shown in FIG. 6, the electron beams of 1.8 MeV (curve A), 2.2 MeV (curve B) and 3 MeV (curve C) were not penetrating enough to cross the entire smaller diameter of the flange (16 mm). The graph in FIG. 6 shows how from 11 mm onwards (x-axis), the energy of the electrons begins to fall sharply. This causes them to lose their sterilizing power and, therefore, there will be a zone -13-, as shown in FIG. 5, which will not be correctly sterilized, and which may come into contact with the product contained in the bag. On the other hand, from 4 MeV onwards (curve D), this zone is sterilized because the energy of the electrons is kept up to 16 mm.

What is claimed is:

1. A combination of a device and a flexible bag to be sterilized, the device configured for sterilization of the flexible bag, comprising:
   the flexible bag;
   a first accelerator that emits an electron beam with energies between 400-500 keV;
   a second accelerator that emits an electron beam with an energy of at least 4 MeV;
   a sterilization zone, wherein the sterilization zone represents a space formed between the first and second accelerators and the flexible bag to be sterilized, such that the sterilization zone is within the electron beams emitted by the first and second accelerators;
   wherein the first and second accelerators are located horizontally adjacent to each other, wherein the first and second accelerators and the flexible bag to be sterilized are located vertically adjacent to each other, and
   wherein a distance between the flexible bag to be sterilized and the first and second accelerators is between 1.5 cm and 7 cm.

2. The combination according to claim 1, wherein said second accelerator emits an electron beam with energies between 4 and 5 MeV.

3. The combination according to claim 2, wherein said second accelerator emits an electron beam with an energy of 4 MeV.

4. The combination according to claim 1, wherein the accelerators are arranged in parallel at the top of above the device and in such a way that the electron beams are emitted downwards, in a direction perpendicular to the ground.

5. The combination according to claim 1, wherein said device is arranged in a radiation-proof area where measures have been taken to contain the radiation emitted by the electron accelerators.

6. The combination according to claim 5, wherein said containment measures are walls and/or a floor which are at least 65-cm thick.

7. The combination according to claim 6, wherein said walls and/or floors are made of lead.

* * * * *